(12) United States Patent
Robinson et al.

(10) Patent No.: US 12,721,755 B2
(45) Date of Patent: Sep. 1, 2026

(54) DRESSINGS WITH ACTIVATED ADHESION

(71) Applicant: KCI Manufacturing Unlimited Company, Westmeath (IE)

(72) Inventors: Timothy Mark Robinson, Shillingstone (GB); Christopher Brian Locke, Bournemouth (GB); Rosella Kendrick, Stourbridge (GB); Benjamin Stokes, Ringwood (GB)

(73) Assignee: KCI Manufacturing Unlimited Conpany, Westmeath (IE)

( * ) Notice: Subject to any disclaimer, the term of this patent is extended or adjusted under 35 U.S.C. 154(b) by 552 days.

(21) Appl. No.: 18/038,961

(22) PCT Filed: Nov. 11, 2021

(86) PCT No.: PCT/IB2021/060450
§ 371 (c)(1),
(2) Date: May 25, 2023

(87) PCT Pub. No.: WO2022/118119
PCT Pub. Date: Jun. 9, 2022

(65) Prior Publication Data

US 2024/0216181 A1 Jul. 4, 2024

Related U.S. Application Data

(60) Provisional application No. 63/121,025, filed on Dec. 3, 2020.

(51) Int. Cl.
*A61F 13/0246* (2024.01)
*A61F 13/02* (2024.01)

(52) U.S. Cl.
CPC ...... *A61F 13/0253* (2013.01); *A61F 13/0289* (2013.01)

(58) Field of Classification Search
CPC .............. A61F 13/0253; A61F 13/0256; A61F 13/0246; A61L 24/043; A61L 15/585;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report/Written Opinion for PCT International Application No. PCT/1B2021/060450, mailed Feb. 22, 2022.
(Continued)

*Primary Examiner* — Philip R Wiest
*Assistant Examiner* — Seth Han

(57) ABSTRACT

A dressing for treating a tissue site is provided herein which may comprise a cover, an adhesive layer coupled to the cover and a tissue interface coupled to the adhesive layer. The dressing may be used to treat the tissue site with negative pressure. The adhesive layer may contain microcapsules containing an adhesive capable of being released upon heat, movement, force and/or sheer to reduce or prevent leakage from the dressing. The microcapsules may be dispersed in the adhesive layer and/or present on the surface of the adhesive layer. Compositions and methods of use are also provided herein.

13 Claims, 4 Drawing Sheets

(58) Field of Classification Search
CPC ....... C09J 7/38; C09J 7/385; A61B 2046/205; B29C 67/24
See application file for complete search history.

(56) References Cited

U.S. PATENT DOCUMENTS

| | | | |
|---|---|---|---|
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,367,332 A | | 2/1968 | Groves |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt |
| 4,940,852 A | | 7/1990 | Chernack |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 5,645,855 A | * | 7/1997 | Lorenz .................. C09J 139/06 602/54 |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 7,846,141 B2 | | 12/2010 | Weston |
| 8,062,273 B2 | | 11/2011 | Weston |
| 8,216,198 B2 | | 7/2012 | Heagle et al. |
| 8,251,979 B2 | | 8/2012 | Malhi |
| 8,257,327 B2 | | 9/2012 | Blott et al. |
| 8,398,614 B2 | | 3/2013 | Blott et al. |
| 8,449,509 B2 | | 5/2013 | Weston |
| 8,529,548 B2 | | 9/2013 | Blott et al. |
| 8,535,296 B2 | | 9/2013 | Blott et al. |
| 8,551,060 B2 | | 10/2013 | Schuessler et al. |
| 8,568,386 B2 | | 10/2013 | Malhi |
| 8,679,081 B2 | | 3/2014 | Heagle et al. |
| 8,834,451 B2 | | 9/2014 | Blott et al. |
| 8,926,592 B2 | | 1/2015 | Blott et al. |
| 9,017,302 B2 | | 4/2015 | Vitaris et al. |
| 9,198,801 B2 | | 12/2015 | Weston |
| 9,211,365 B2 | | 12/2015 | Weston |
| 9,289,542 B2 | | 3/2016 | Blott et al. |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2014/0163491 A1 | | 6/2014 | Schuessler et al. |
| 2015/0080788 A1 | | 3/2015 | Blott et al. |
| 2018/0030321 A1 | * | 2/2018 | Tunius .................... A61P 17/02 |
| 2019/0060127 A1 | * | 2/2019 | Locke ..................... A61F 13/05 |
| 2019/0262146 A1 | * | 8/2019 | Mccarthy .................. A61F 2/78 |
| 2020/0246192 A1 | * | 8/2020 | Hoggarth ............ A61F 13/0246 |
| 2022/0315812 A1 | * | 10/2022 | Richter .................. C08L 63/00 |

FOREIGN PATENT DOCUMENTS

| | | | | | |
|---|---|---|---|---|---|
| AU | 755496 | B2 | | 12/2002 | |
| CA | 2005436 | A1 | | 6/1990 | |
| CN | 1427771 | A | | 7/2003 | |
| DE | 26 40 413 | A1 | | 3/1978 | |
| DE | 43 06 478 | A1 | | 9/1994 | |
| DE | 29 504 378 | U1 | | 9/1995 | |
| EP | 0100148 | A1 | | 2/1984 | |
| EP | 0117632 | A2 | | 9/1984 | |
| EP | 0161865 | A2 | | 11/1985 | |
| EP | 0358302 | A2 | | 3/1990 | |
| EP | 1018967 | A1 | | 7/2000 | |
| GB | 692578 | A | | 6/1953 | |
| GB | 2133374 | A | * | 7/1984 | ............. B01J 13/18 |
| GB | 2195255 | A | | 4/1988 | |
| GB | 2 197 789 | A | | 6/1988 | |
| GB | 2 220 357 | A | | 1/1990 | |

(56) References Cited

FOREIGN PATENT DOCUMENTS

| | | | |
|---|---|---|---|
| GB | 2 235 877 | A | 3/1991 |
| GB | 2 329 127 | A | 3/1999 |
| GB | 2 333 965 | A | 8/1999 |
| JP | S6060173 | A | 4/1985 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 92/16290 | A1 | 10/1992 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2018/226328 | A1 | 12/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjom et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

DRESSINGS WITH ACTIVATED ADHESION

CROSS-REFERENCE TO RELATED APPLICATIONS

This application claims the benefit of priority to U.S. Provisional Application No. 63/121,025, filed on Dec. 3, 2020, which is incorporated herein by reference in its entirety.

TECHNICAL FIELD

The invention set forth in the appended claims relates generally to tissue treatment systems and more particularly, but without limitation, to improved dressings having less leakage.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients. For example, a cover in a dressing can lift off difficult to seal areas, such as hips, abdomens, skin folds, areas with friction and articulating joints, causing leaks.

BRIEF SUMMARY

New and useful systems, apparatuses, dressings and methods for making dressings, and methods for treating tissue sites in a negative-pressure therapy environment are set forth in the appended claims. Illustrative embodiments are also provided to enable a person skilled in the art to make and use the claimed subject matter.

Dressings, particularly low leak dressings, that can remain on a wound for 7 days or more may encounter problems while a patient is trying to return to normality. An increasing number of portable negative-pressure therapy devices are being sent home with patients to allow patients to return home or to work carrying their device while receiving treatment. However, portability in turn allows for more movement, so more difficult to seal areas, such as articulating areas which the drape is attached to may cause the drape to lift off due to its rigidity, which may be causing leaks in the dressing. Current practice is to add more drape to patch leaks, however some areas of the dressing around skin folds, body contours or articulating areas of the body are difficult to seal due to frequent movement. Leaks in the home environment may cause both annoyance and/or non-compliance, and may require a healthcare professional to visit the patient to correctly patch up the leak on their dressing causing a delay or break in therapy.

Thus, in some embodiments, dressings having low leakage to substantially no leakage are provided herein.

More generally, in some embodiments, a dressing is provided comprising a cover, an adhesive layer coupled to the cover, and a tissue interface coupled to the adhesive layer. Microcapsules comprising an adhesive encapsulated by a polymer can be embedded in the adhesive layer and/or present on a surface of the adhesive layer.

Alternatively, other example embodiments may include a method of making a dressing provided herein comprising embedding microcapsules into the adhesive layer and/or applying a microcapsule dispersion to a surface of the adhesive layer; and coupling the adhesive layer to at least part of a side of the cover.

Alternatively, other example embodiments may include a method of treating a tissue site with negative pressure comprising applying a dressing provided herein to a tissue site; sealing the dressing to epidermis adjacent to the tissue site; fluidly coupling the dressing to a negative-pressure source; and applying negative pressure from the negative-pressure source to the dressing.

A composition is also provided herein, wherein some example embodiments include a dispersing agent, e.g. a first adhesive or polymer, having microcapsules dispersed therein. The microcapsules may comprise a second adhesive, which may be the same or different from the first adhesive, encapsulated by a polymer. The composition may be a sprayable or brushable composition to help minimize and eliminate leaks from wound dressings.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Therapy System

Figure 1:
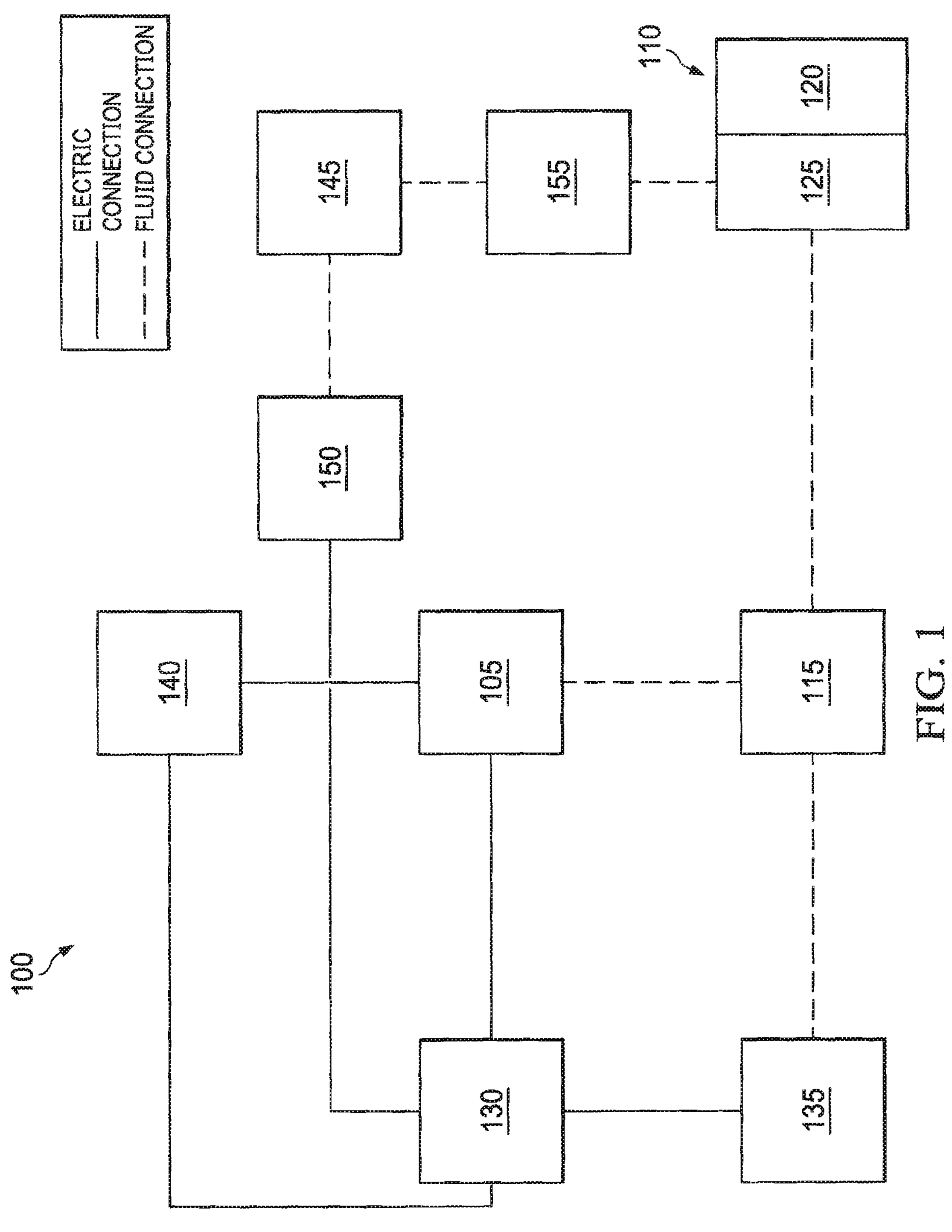
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source [such as a positive-pressure source 150, a negative-pressure source such as the negative-pressure source 105, or both] in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

Tissue Interface

As discussed previously, a dressing 110 provided herein may comprise a tissue interface 120. The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Cover

In some embodiments, the cover 125 may provide a bacterial barrier and protection from physical trauma. The cover 125 may have a first and a second side. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials and may be in the form of a film: polyurethane (PU), such as hydrophilic polyurethane; cellulosics, such as a cellulosic ester; hydrophilic polyamides; polyvinyl alcohol; polyvinyl pyrrolidone; hydrophilic acrylics, such as a hydroxyl and carboxyl-containing acrylic; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

Adhesive Layer

Figures 1A, 1B:
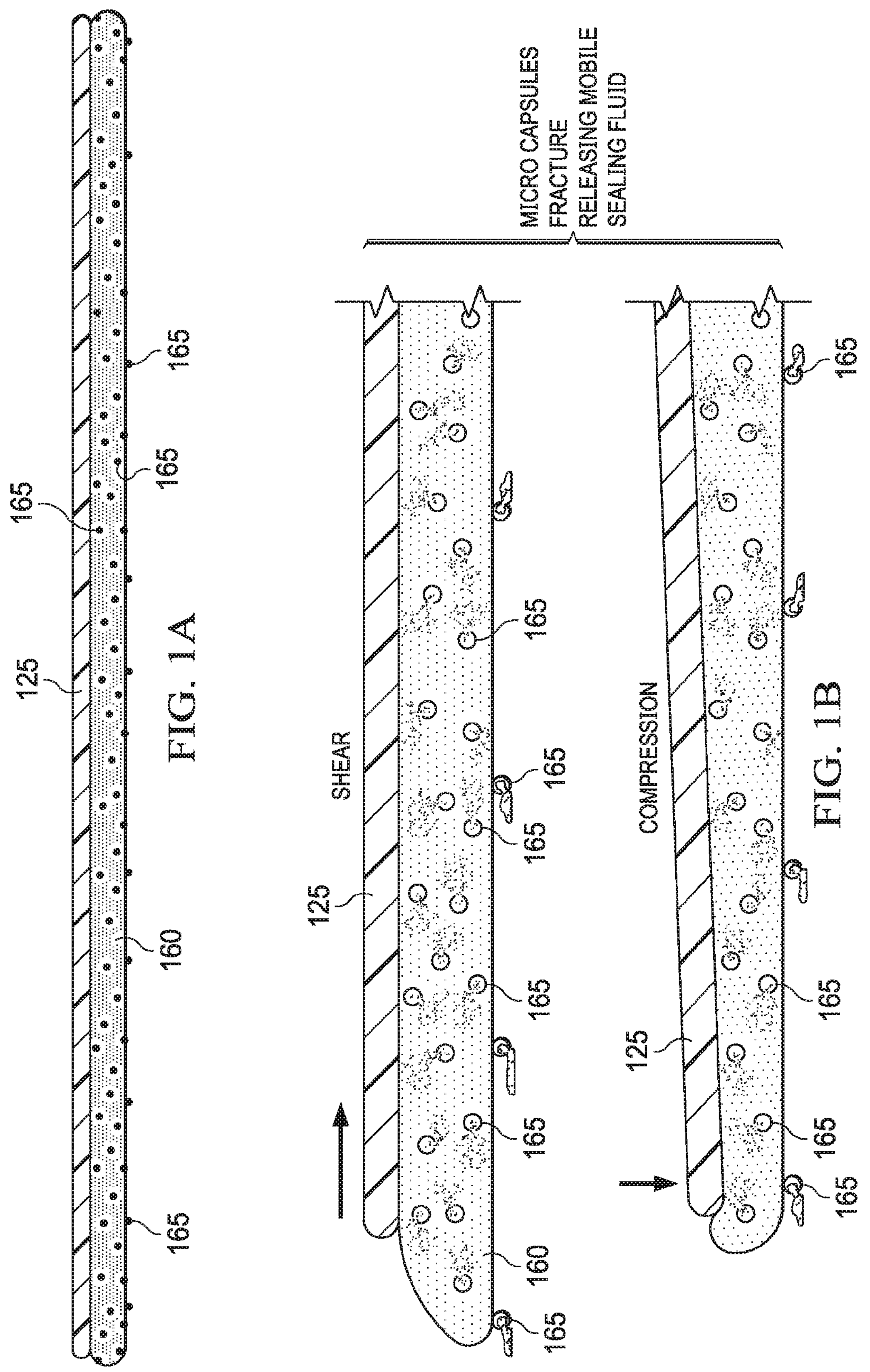
FIG. 1A is a representation illustrating details of a dressing that may be associated with example embodiments of the therapy system of FIG. 1.
FIG. 1B is a representation illustrating examples of adhesive release mechanisms (shear and/or compression) in an example dressing that may be associated with example embodiments of the therapy system of FIG. 1.

An attachment device may be used to attach the cover 125 to an attachment surface, such as undamaged epidermis, a gasket, or another cover. The attachment device may take many forms. In some embodiments, the attachment device may be an adhesive layer 160 comprising a first adhesive coupled to at least part of a first side of the cover 125 as shown in FIGS. 1A and 1B. The adhesive layer may be directly or indirectly coupled to at least part of a first side of the cover 125. In the example of FIGS. 1A and 1B, the adhesive layer 160 is directly coupled to a first side of the cover 125.

The first adhesive may comprise an acrylic adhesive, a polyurethane adhesive, a rubber-based adhesive, a hydrocolloid adhesive or a combination thereof. For example, the first adhesive may be a medically-acceptable, pressure-sensitive adhesive (PSA), such a medium-tack, high-tack or combination thereof PSA. Commercial examples of PSAs with different tack measurements include LOCTITE® DURO-TAK adhesives from Henkel AG & Co. and Aroset™ adhesives from Ashland Inc.

The adhesive layer 160 comprising the first adhesive may be configured to bond the cover 125 to epidermis around a tissue site or wound. In some embodiments, for example, some or all of the first and/or second side of the cover 125 may be coated with the adhesive layer 160, which may have a coating weight of about 25-65 grams per square meter (g.s.m.). Thicker adhesives, or combinations of adhesives, may be applied to further improve the seal and reduce leaks. Other example embodiments of an attachment device may include a double-sided tape, paste, hydrocolloid, hydrogel, silicone gel, or organogel.

Additionally, the adhesive layer 160 may also comprise microcapsules 165. As shown in the example of FIG. 1A, in some embodiments, the microcapsules are dispersed, embedded or suspended in the adhesive layer 160. Additionally or alternatively, the microcapsules 165 may be present on all or a portion of a surface of the adhesive layer 160.

The microcapsules 165 comprise a second adhesive encapsulated by a polymer. The second adhesive may be the same or different from the first adhesive. The second adhesive may take many forms, such as a solid, liquid, or semi-solid, such as a gel. In particular embodiments, the second adhesive is a gel, such as a hydrogel, a polyurethane gel or an acrylic gel. In further particular embodiments, the second adhesive may comprise polyethylene glycol (PEG) microcapsules. The PEG may range in molecular mass of about 400 g/mol to about 2500 g/mol, about 500 g/mol to about 2000 g/mol, and particularly about 600 g/mol to about 1500 g/mol.

Additionally or alternatively, the second adhesive may be a low viscosity adhesive. A low viscosity adhesive as used herein has a viscosity of 200,000 mPa·s (millipascal second) or less as measured by a cone and plate viscometer. A cone and plate viscometer is a standard test for dynamic viscosity measurements and is well-known in the art. Examples of low viscosity adhesives include aqueous polymer emulsions, low molecular mass polymer solutions, low molecular mass, low $T_g$/melting/softening polymers, where these polymers may include polyvinyl acetate and other vinyl esters, an acrylic, a polyurethane, a silicone, and a block copolymer elastomer.

Additionally or alternatively, the second adhesive may be a superabsorbent polymer (SAP). Superabsorbent polymers can absorb and retain large amounts of liquid relative to its own mass and are well-known. The total absorbency and swelling capacity are controlled by the type and degree of cross-linkers used to make the gel. Low-density cross-linked SAPs generally have a higher absorbent capacity and swell to a larger degree. These types of SAPs also have a softer and stickier gel formation. High cross-link density polymers exhibit lower absorbent capacity and swell, but the gel strength is firmer and can maintain particle shape even under modest pressure. Superabsorbent polymers include, but are not limited to, cross-linked hydrophillic polymers: cellulose salt such as sodium carboxymethyl cellulose (CMC), poly (acrylic acid) (PAA), poly(methacrylic acid) (PMAA), polyacrylamide, and acrylic polymers having acid groups (2-acrylamido-2-methyl propane sulfonic acid) [AMPS].

Additionally or alternatively, the second adhesive may be able to undergo a phase change. For example, the second adhesive may initially be present in a solid, semi-solid or gel state and then become a liquid state, due to heat. A solid or semi-solid state may be simpler to encapsulate and a liquid better suited to flow and seal a leak.

Additionally or alternatively, the second adhesive may be a moisture-activated adhesive, such as polyisocyanate, an isocyanate-terminated polymer, and an alkoxy silane-terminated polymer.

The polymer used to encapsulate the second adhesive (i.e. the encapsulating or coating polymer) may comprise PVOH, EVA, a pyrrolidone ethylene and acetate co-polymer, an ethylene-ethylene oxide co-polymer, a polyurethane, a gelatin, and a cellulose salt and ester.

The microcapsules 165 provided herein may be about 0.5 micron to about 100 microns in diameter, or about 0.5 to about 50 microns in diameter, or about 1 micron to about 20 microns in diameter, or about 1 micron to about 6 microns in diameter. The microcapsules 165 provided herein may account for about 5% to about 20% of the first adhesive thickness.

The microcapsules 165 provided herein may be a variety of shapes, for example, spherical, rod or fiber-shaped, or a mixture of shapes.

As shown in the example of FIG. 1B, the microcapsules 165 provided herein may be capable of fracture upon movement (shear) or a force (compression) equal to or greater than 3N. Once the microcapsules are fractured, the second adhesive is released from the microcapsule and may reduce or substantially prevent leakage from a dressing, such as a wound dressing. In some embodiments, the microcapsules 165 can fracture at different force values. For example, some microcapsules 165 present in the dressing may fracture at >3N, >4N, >5N and/or >6N.

Additionally or alternatively, the microcapsules 165 may be capable of fracture upon the second adhesive undergoing a phase change, for example from a solid, semi-solid or gel to a liquid. For example, in some embodiments, a low-melt adhesive (i.e. having a melting range of about 25° C. to about 45° C.) may be used as a second adhesive. Heat from a subject's body or external source may melt the second adhesive to a more liquid state. For example, if the second adhesive/leak sealer were a polyethylene glycol (PEG) of about 1000 molecular mass it would be in a solid state until about 33° C. When in contact with body heat (e.g. after drape placement) or an external source of heat it will melt, expand and put increased stress on the encapsulating polymer shell making it more sensitive to shear forces (i.e. the microcapsule has been effectively primed and enable a more robust microcapsule to be made reducing accidental triggering of the release mechanism before the drape is placed). Once released the PEG would be mobile and seal leaks and may also be designed to swell the drape adhesive, increasing its stickiness and volume.

In addition to a second adhesive the microcapsules 165 may comprise further agents to help identify and prevent leakages, such as a coloring agent or dye (which may be a UV-activated dye). Once the microcapsules 165 are fractured, a coloring agent can be released along with the second adhesive to visually identify the movement of the mobile second adhesive. Additionally or alternatively the adhesive layer 160 may contain separate microcapsules encapsulating the coloring agent, which are also capable of fracturing upon heat, movement (shear), and/or compression (force).

Although not depicted in FIG. 1A, the tissue interface 120 can also be indirectly coupled to the adhesive layer 160. That is to say, additional layers or "materials" may be present in the dressing between the adhesive layer 160 and the tissue interface 120.

Methods of Making

A method of making the microcapsules 165, i.e. microencapsulation, is also provided herein. Microencapsulation is the process by which solid, liquid or gel core materials are encased in tiny shells or capsules. The second adhesive provided herein may be microencapsulated with a suitable polymer provided herein. A variety of microencapsulation methods are well-known to those of skill in the art. For example, the microcapsules 165 may be made by pan-coating/dry tumbling, spray drying or centrifugal extrusion with vibration methods. See for example, SouthWest Research Institute—Chemical encapsulation Techniques; Vladisavljevic G. (2015) Encapsulation Techniques. In: Drioli E., Giorno L. (eds) Encyclopedia of Membranes. Springer, Berlin, Heidelberg. Lubrizol Life Science.

For example, in the pan-coating microencapsulation technique, the second adhesive (e.g. PEG powder) can be added to a pan tumbler and during the tumbling action a coating polymer (e.g. any of the encapsulating polymers described herein) can be slowly added, forming a microcapsule.

Additionally or alternatively, using the spray drying example, a dispersion of the second adhesive (e.g. PEG) and the coating polymer can be dispersed in water or solvent, such as a low molecular mass alcohol or ketone or blend which may include water, and sprayed into a hot gas stream where the solvent evaporates resulting in a microcapsule.

Additionally or alternatively, the second adhesive (e.g. PEG) may be dispersed into a polymer melt or solution and then extruded through concentric dies which also vibrate forming droplets in the emerging extrusion vibrating nozzle. The melt is cooled, or if a solution, the solvent is evaporated, to form the solid microencapsulated second adhesive. It is expected that the molten second adhesive (e.g. PEG) and coating polymer will cool and contract together, maintaining a close tight fit between the two materials. As noted herein, the microcapsules 165 may take a variety of shapes, such as spherical, or hollow rod or fiber, or a mixture of shapes. Generally, the rod-shaped microcapsules are more prone to fracture and they can be made through the melt extrusion process, or one can roll/press sphere-shaped microcapsules to make them rod-shaped and thus more prone to fracture. Because the rod shape may be more sensitive to movement and likely to rupture, they may be used to provide different degrees of release of the second adhesive (small to large movements may result in microcapsule rupture depending on the shape/mix used).

In some embodiments, once the microcapsules 165 are made they may be dispersed in a suitable coating media, such as non-polar solvent, to form a microcapsule dispersion. Examples of non-polar solvents include toluene, an alkane and a cycloalkane.

Additionally, a method of making a dressing is also provided herein which may comprise applying the microcapsule dispersion to a surface of the adhesive layer 160. The microcapsule dispersion may be applied by spraying or off-set printing (e.g. the microcapsule dispersion may be applied to a film carrier which is then brought into contact with a surface of the adhesive layer 160) where pattern coating may permit the surface to have zones of the first adhesive and microcapsule exposed.

Additionally or alternatively to applying the microcapsule dispersion to a surface of the adhesive layer 160, microcapsules 165 may be mixed in the first adhesive to form the adhesive layer 160, such that the microcapsules 165 are embedded or suspended or dispersed in the adhesive layer 160.

The method of making the dressing may also comprise applying the adhesive layer 160 to at least a portion of a side (such as a first side) of the cover 125. The adhesive layer 160 containing or not containing the microcapsules 165 may be applied to the cover 125 and then in some embodiments the microcapsule dispersion may be applied to the adhesive layer 160.

Additionally, the method of making the dressing may also comprise coupling the adhesive layer 160 or a portion of the adhesive layer 160 to the tissue interface 120.

NPWT

In additional embodiments, a method of treating a tissue site with negative pressure is provided comprising: applying a dressing 110 to a tissue site; sealing the dressing 110 to epidermis adjacent to the tissue site; fluidly coupling the dressing 110 to a negative-pressure source; and applying negative pressure from the negative-pressure source to the dressing 110.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment. In some embodiments, the dressing 110 may be applied to dispose at least part of the dressing 110 across an edge of the tissue site. Additionally, a second tissue interface may be disposed between the dressing 110 and the tissue site.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
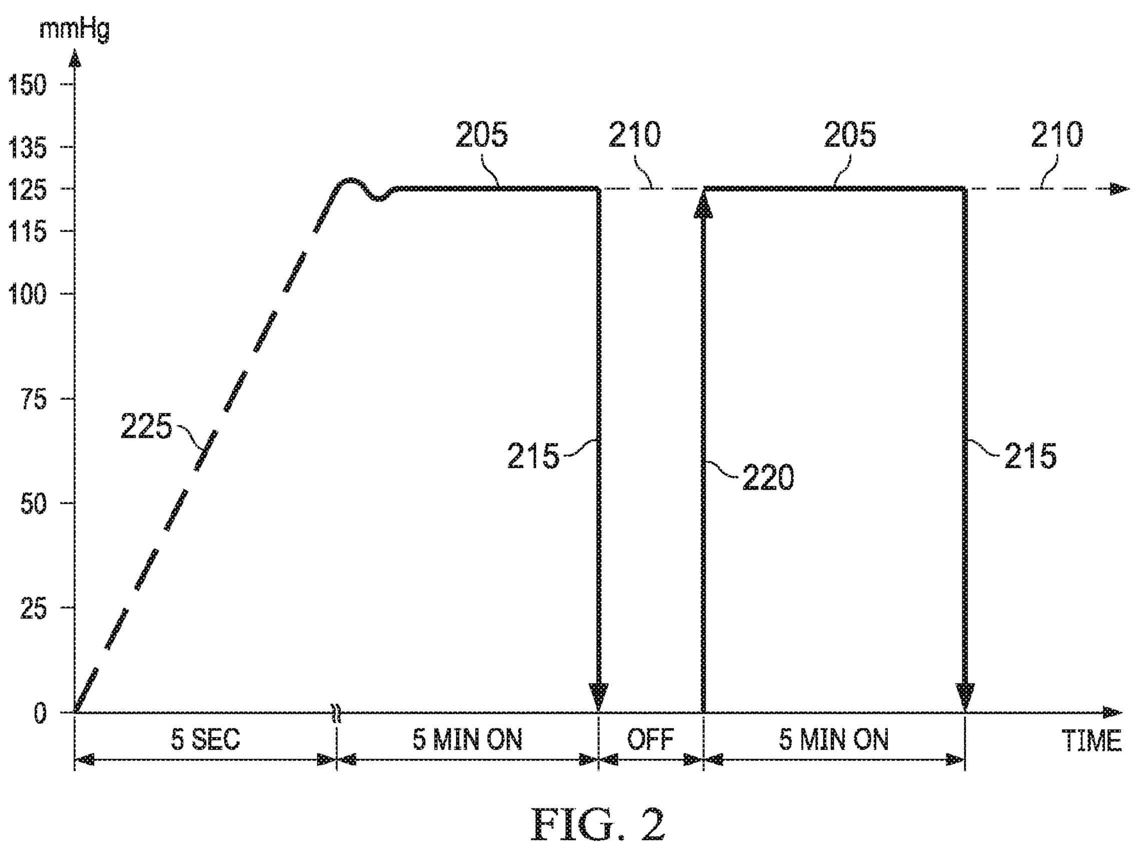
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 130. In some embodiments, the controller 130 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time and the y-axis represents negative pressure generated by the negative-pressure source 105 over time. In the example of FIG. 2, the controller 130 can operate the negative-pressure source 105 to cycle between a target pressure and atmospheric pressure. For example, the target pressure may be set at a value of 135 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
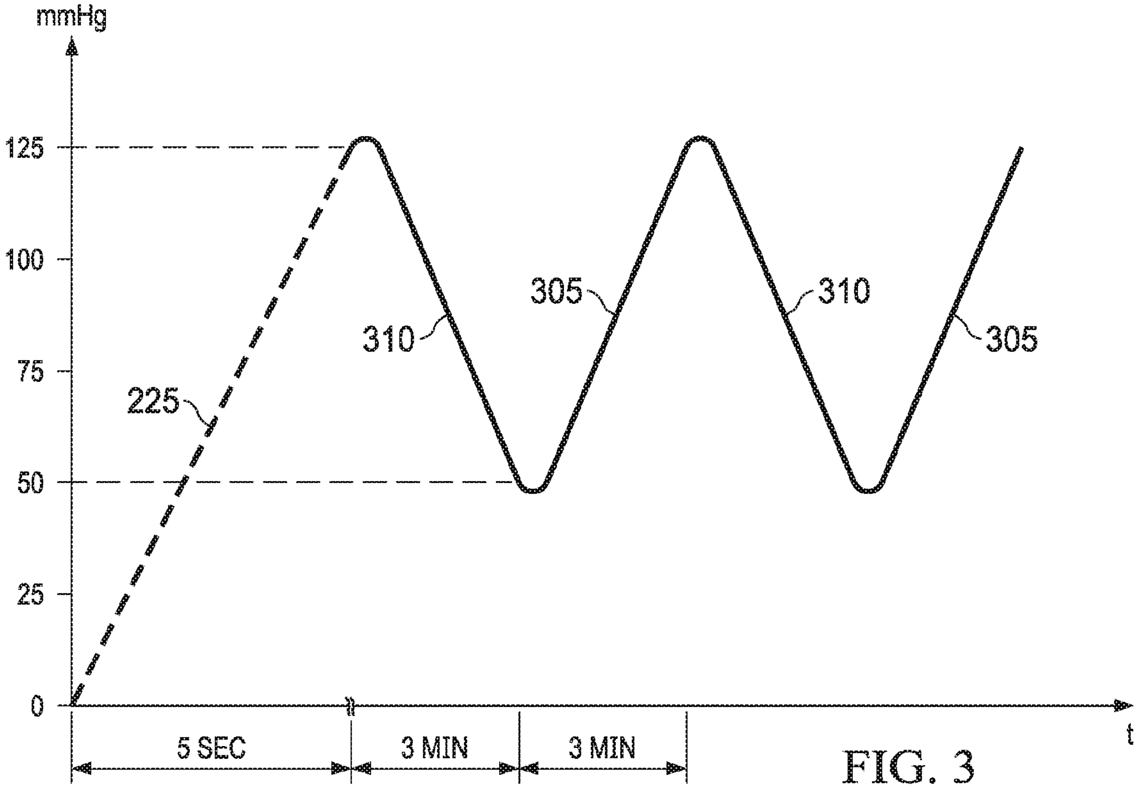
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 135 mmHg with a rise time 305 set at a rate of +25 mmHg/min. and a descent time 310 set at −25 mmHg/min. In other embodiments of the therapy system 100, the triangular waveform may vary between negative pressure of 25 and 135 mmHg with a rise time 305 set at a rate of +30 mmHg/min and a descent time 310 set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
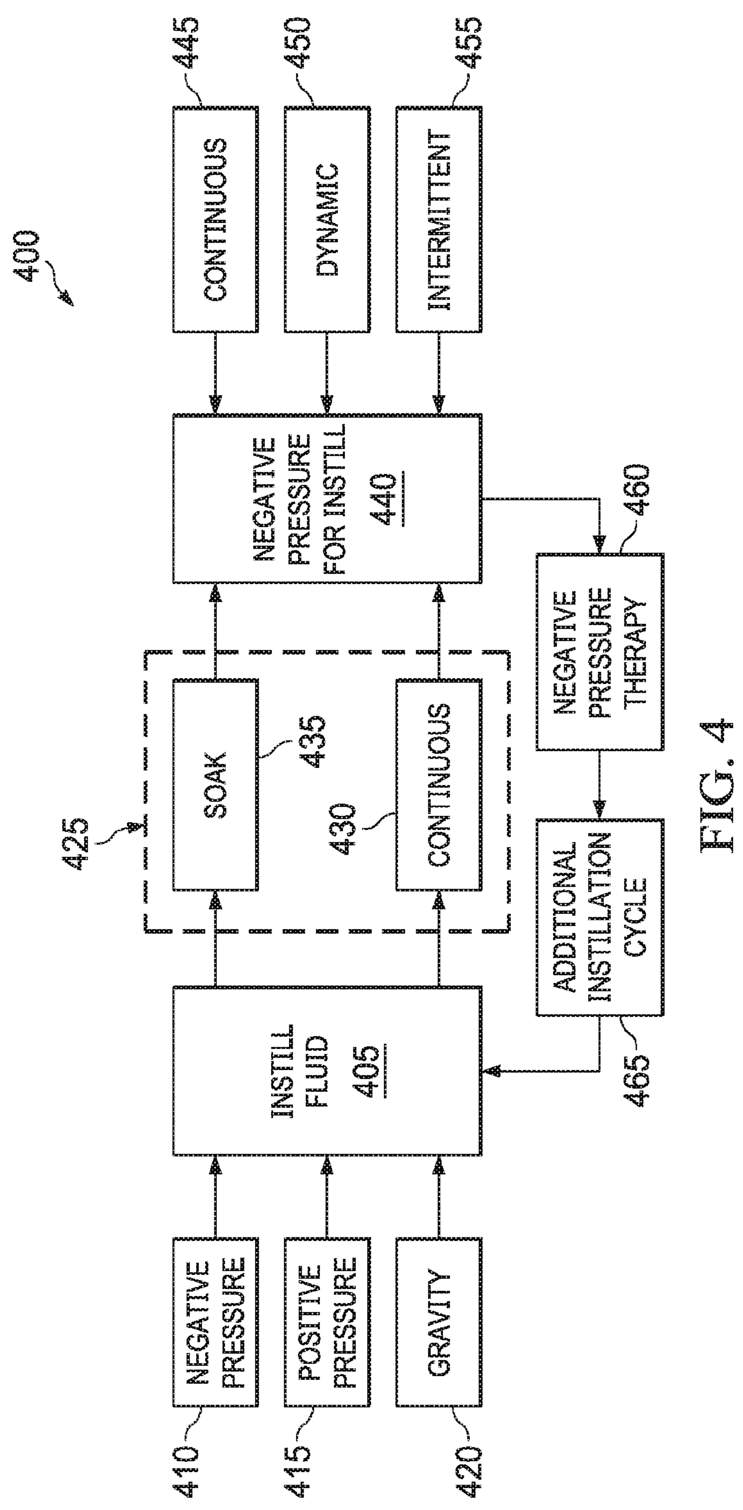
FIG. 4 is a chart illustrating details that may be associated with an example method of operating the therapy system of FIG. 1.

FIG. 4 is a chart illustrating details that may be associated with an example method 400 of operating the therapy system 100 to provide negative-pressure treatment and instillation treatment to the tissue interface 120. In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution, as indicated at 405. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120, as indicated at 410. In some embodiments, solution may be instilled to a tissue site by applying a positive pressure from the positive-pressure source 160 to move solution from the solution source 145 to the tissue interface 120, as indicated at 415. Additionally or alternatively, the solution source 145 may be elevated to a height sufficient to allow gravity to move solution into the tissue interface 120, as indicated at 420.

The controller 130 may also control the fluid dynamics of instillation at 425 by providing a continuous flow of solution at 430 or an intermittent flow of solution at 435. Negative pressure may be applied to provide either continuous flow or intermittent flow of solution at 440. The application of negative pressure may be implemented to provide a continuous pressure mode of operation at 445 to achieve a continuous flow rate of instillation solution through the tissue interface 120, or it may be implemented to provide a dynamic pressure mode of operation at 450 to vary the flow rate of instillation solution through the tissue interface 120. Alternatively, the application of negative pressure may be implemented to provide an intermittent mode of operation at 455 to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied at 460. The controller 130 may be utilized to select a mode of operation and the duration of the negative pressure treatment before commencing another instillation cycle at 465 by instilling more solution at 405.

Composition

In additional embodiments, a composition for reducing and/or substantially preventing leakage from the dressing is also provided. The composition may improve the seal and/or adhesion of a wound cover especially in areas of the body that are difficult to seal because of body movement. The composition may be able to bond to the subject's skin, the adhesive used in the adhesive layer 160, and/or the cover 125. The composition may comprise a dispersing agent (also known as a carrier or media) and microcapsules, as provided herein, dispersed in the dispersing agent. The dispersing agent may be a first adhesive, such as any first adhesive discussed herein. For example, an acrylic adhesive. Additionally or alternatively, the dispersing agent may be one or more polymers that can be capable of drying to form a dry film that may also act as a skin protector. Examples of suitable polymers include, but are not limited to, acrylics, vinyl acetates, vinyl alcohols, urethanes, silicones, vinyl pyrrolidones, ethylene oxides and cellulosics.

The composition may take a variety of forms. For example, the composition may be a sprayable composition, such as a liquid, where one can spray the composition in areas on the skin (e.g. a skin prep) or cover needed to reduce or prevent leakage. The sprayable composition may be contained in a pump or aerosol container. Additionally or alternatively, the composition may be a brushable composition, such as a gel or semi-solid, where one can brush the composition onto areas of the skin (e.g. a skin prep) or cover needed to reduce or prevent leakage. A gel or semi-solid composition may comprise a polyurethane or a silicone polymer and may be solventless, or use organic solvents, such as ethanol or isopropyl alcohol, and water (blends), where the polymers may be vinyl pyrrolidones, ethylene oxides, and/or cellulosic esters.

The system, dressing, and methods described herein may provide significant advantages. The dressing may utilize microencapsulation technology to dynamically improve the seal and adhesion of a wound cover. In one example, friction can cause the release of additional low viscosity adhesive material which can seal micro-leaks and improve the dressing performance, but which is not required in applications where movement and forces are not exerted, thus not causing unnecessary trauma for non-mobile patients. The dressing may remain intact while the patient is mobile, which utilizes the patient's own movement to improve and seal the dressing if there is a chance it might lift off the skin or a small leak may propagate into a larger leak. A second adhesive may be microencapsulated and mixed into a drape acrylic adhesive and activated by the encapsulate breaking down and releasing the second adhesive due to movement. In some embodiments, the released second adhesive may be of a very low viscosity nature such as a hydrogel. They hydrogel may assist with sealing creases and small leak pathways, but may readily dry out and become more viscous due to evaporation. The second adhesive may also be an acrylic or polyurethane gel which may also change viscosity with time and evaporation. The microcapsules are intended to break and burst with movement, friction, and/or sheer. As such they may be triggered to release automatically due to movement or may be manually triggered to release if subjected to a force (e.g. a force greater than 3N). Thus, the user/patient may force release in areas where they perceive there to be a leak.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

EXAMPLES

Example 1: Procedure for making microcapsules: the core of the microcapsule is made by the spray drying process. The cores are collected and added to a fluidized bed which is then sprayed with the encapsulant in a solvent, whereupon the solvent dries to leave the formed microcapsule which is collected for use.

Example 2: Procedure for making dressing with microcapsules mixed into drape adhesive: The adhesive may be formed from an acrylic polymer suspended in a solvent to which is added the microcapsules through mixing which may be done in a reactor/mixer fitted with a mixing rotor. The adhesive is then fed horizontally to a coating line where the film (may be polyurethane) is coated with the adhesive using a knife over roll technique. The adhesive coated film is dried through the effect of forced heated air passing over it in a tunnel oven that may be of the air flotation type. The adhesive is cooled and laminated to a release layer before being wound into a coil.

Example 3: Procedure for making microcapsule dispersion and spraying onto drape adhesive: The drape film is coated with adhesive per Example 2, without the addition of microencapsulated additive. Just after leaving the drying oven the microcapsules are sprayed onto the adhesive either as a dry spray or suspended in a continuous phase such as water or water/solvent mix (a dispersion). If the latter then a further drying stage is required before the adhesive coated film is laminated onto a release film layer.

What is claimed is:

1. A dressing comprising:
a cover having a first side and a second side;
an adhesive layer comprising a first adhesive coupled to at least part of the first side of the cover;
wherein microcapsules comprising a second adhesive encapsulated by a polymer are embedded in or present on a surface of the adhesive layer; and
a tissue interface coupled to the adhesive layer.

2. The dressing of claim 1, wherein the cover comprises a polyurethane film, a polyether block amine copolymers (PEBAX) film, a polyamide film, a cellulose ester film, a hydroxyl and carboxyl containing acrylic film, or a polyvinyl alcohol film.

3. The dressing of claim 1, wherein the first adhesive comprises an acrylic adhesive, a polyurethane adhesive, a rubber-based adhesive, a hydrocolloid adhesive or a combination thereof.

4. The dressing of claim 1, wherein the second adhesive comprises a low viscosity adhesive and/or a superabsorbent.

5. The dressing of claim 1, wherein the second adhesive comprises a hydrogel, a polyurethane gel or an acrylic gel.

6. The dressing of claim 1, wherein the second adhesive comprises polyethylene glycol of 400 to 2500 g/mol.

7. The dressing of claim 1, wherein the polymer comprises PVOH, EVA, pyrrolidone ethylene and acetate co-polymers, ethylene-ethylene oxide co-polymers, a polyurethane, a gelatin, and a cellulose salt and ester.

8. The dressing of claim 1, wherein the microcapsules are capable of fracture upon movement (shear) or a force (compression) equal to or greater than 3N.

9. The dressing of claim 1, wherein the tissue interface comprises a manifold comprising open cell reticulated polyurethane foam.

10. A method of treating a tissue site with negative pressure, the method comprising:

applying a dressing to a tissue site, the dressing comprising:

a cover having a first side and a second side;

an adhesive layer comprising a first adhesive coupled to at least part of the first side of the cover;

wherein microcapsules comprising a second adhesive encapsulated by a polymer are embedded in or present on a surface of the adhesive layer; and a tissue interface coupled to the adhesive layer;

sealing the dressing to epidermis adjacent to the tissue site;

fluidly coupling the dressing to a negative-pressure source; and applying negative pressure from the negative-pressure source to the dressing.

11. The method of claim 10, wherein applying the dressing comprises disposing at least part of the dressing across an edge of the tissue site.

12. The method of claim 10, further comprising fluidly coupling a fluid container between the dressing and the negative-pressure source, and transferring exudate from the dressing to the fluid container.

13. The method of claim 10, further comprising applying a second tissue interface between the dressing and the tissue site.

* * * * *